(12) United States Patent
Gerrans et al.

(10) Patent No.: US 10,561,305 B2
(45) Date of Patent: Feb. 18, 2020

(54) BODY CAVITY DILATION SYSTEM

(71) Applicants: Lawrence J. Gerrans, San Anselmo, CA (US); Peter Christensen Baker, Ross, CA (US)

(72) Inventors: Lawrence J. Gerrans, San Anselmo, CA (US); Peter Christensen Baker, Ross, CA (US)

(73) Assignee: Sanovas Intellectual Property, LLC

(*) Notice: Subject to any disclaimer, the term of this patent is extended or adjusted under 35 U.S.C. 154(b) by 871 days.

(21) Appl. No.: 14/755,609

(22) Filed: Jun. 30, 2015

(65) Prior Publication Data
US 2017/0000981 A1 Jan. 5, 2017

(51) Int. Cl.
*A61B 1/00* (2006.01)
*A61B 1/05* (2006.01)
*A61M 29/00* (2006.01)
*A61B 18/00* (2006.01)

(52) U.S. Cl.
CPC .............. *A61B 1/05* (2013.01); *A61M 29/00* (2013.01); *A61B 2018/0091* (2013.01)

(58) Field of Classification Search
CPC .................................................. A61M 29/00
USPC ................................ 606/198, 196, 199, 109
See application file for complete search history.

(56) References Cited

U.S. PATENT DOCUMENTS

| | | | |
|---|---|---|---|
| 5,458,573 A * | 10/1995 | Summers | A61M 25/0119 604/101.04 |
| 5,575,771 A | 11/1996 | Walinsky | |
| 5,591,194 A | 1/1997 | Berthiaume | |
| 5,846,259 A | 12/1998 | Berthiaume | |
| 6,126,649 A | 10/2000 | VanTassel et al. | |
| 7,727,226 B2 | 6/2010 | Chang et al. | |
| 7,854,744 B2 | 12/2010 | Becker | |
| 8,282,667 B2 | 10/2012 | Drontle et al. | |
| 8,491,568 B2 | 7/2013 | Schertiger | |
| 2003/0135230 A1* | 7/2003 | Massey | A61B 1/12 606/190 |
| 2005/0124937 A1* | 6/2005 | Kick | A61B 17/3417 604/164.1 |
| 2011/0282251 A1* | 11/2011 | Baker | A61B 17/24 601/2 |
| 2012/0062714 A1* | 3/2012 | Liu | G06T 7/75 348/65 |
| 2012/0071856 A1 | 3/2012 | Goldfarb et al. | |
| 2013/0066358 A1* | 3/2013 | Nalluri | A61F 11/002 606/199 |

(Continued)

FOREIGN PATENT DOCUMENTS

EP 0935974 A1 8/1999

*Primary Examiner* — Alexandra L Newton
*Assistant Examiner* — Rynae Boler
(74) *Attorney, Agent, or Firm* — Forge IP, PLLC

(57) ABSTRACT

A system for dilating a body cavity with a device including a series of elongated members, each having a central channel and increasing outer diameters where the members are positioned one over the other such that the members are advanced into the body cavity to incrementally dilate the body cavity. The central channels of each member allow for various procedures to be performed including, for example, the application of wireless energy (e.g., ultrasonic) to the body cavity, the introduction of an irrigating fluid and aspiration from the body cavity, and the introduction of a drug to the body cavity.

25 Claims, 16 Drawing Sheets

(56) References Cited

U.S. PATENT DOCUMENTS

| | | | |
|---|---|---|---|
| 2013/0072958 A1* | 3/2013 | Ressemann | A61B 17/24 606/199 |
| 2013/0092173 A1* | 4/2013 | Alexander | A61B 1/00108 128/207.18 |
| 2013/0165873 A1 | 6/2013 | Morriss et al. | |
| 2014/0277072 A1 | 9/2014 | Suehara | |
| 2016/0206347 A1* | 7/2016 | Bar | A61M 29/00 |
| 2017/0348516 A1* | 12/2017 | Chang | A61M 25/0147 |

* cited by examiner

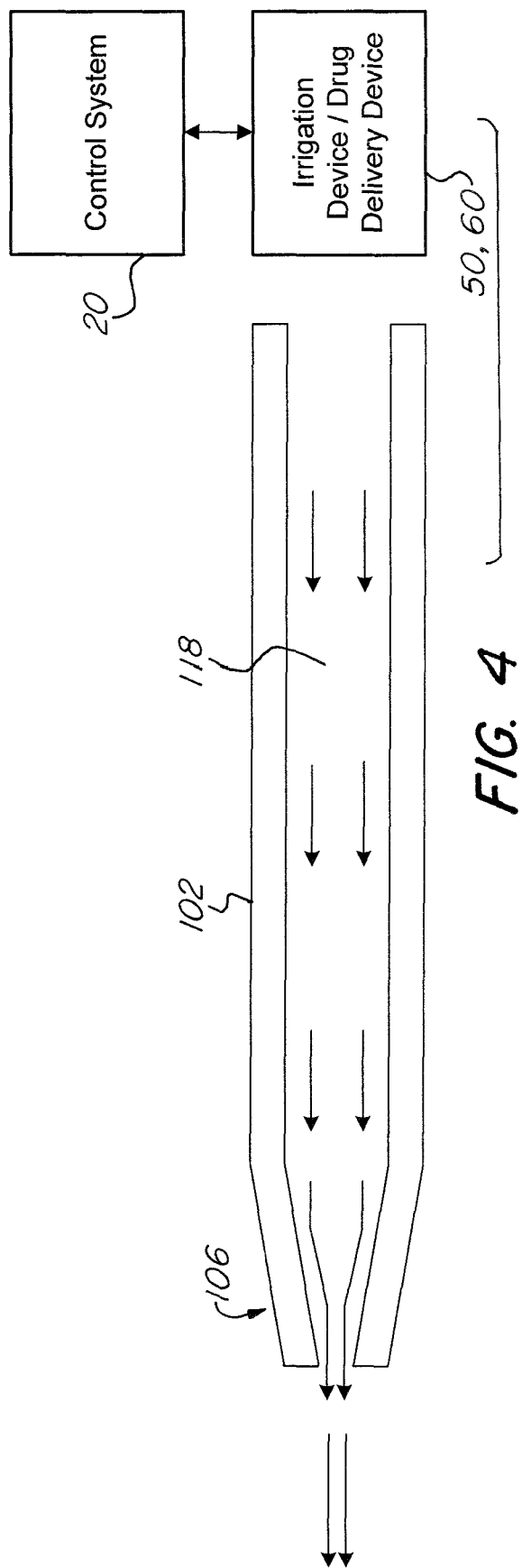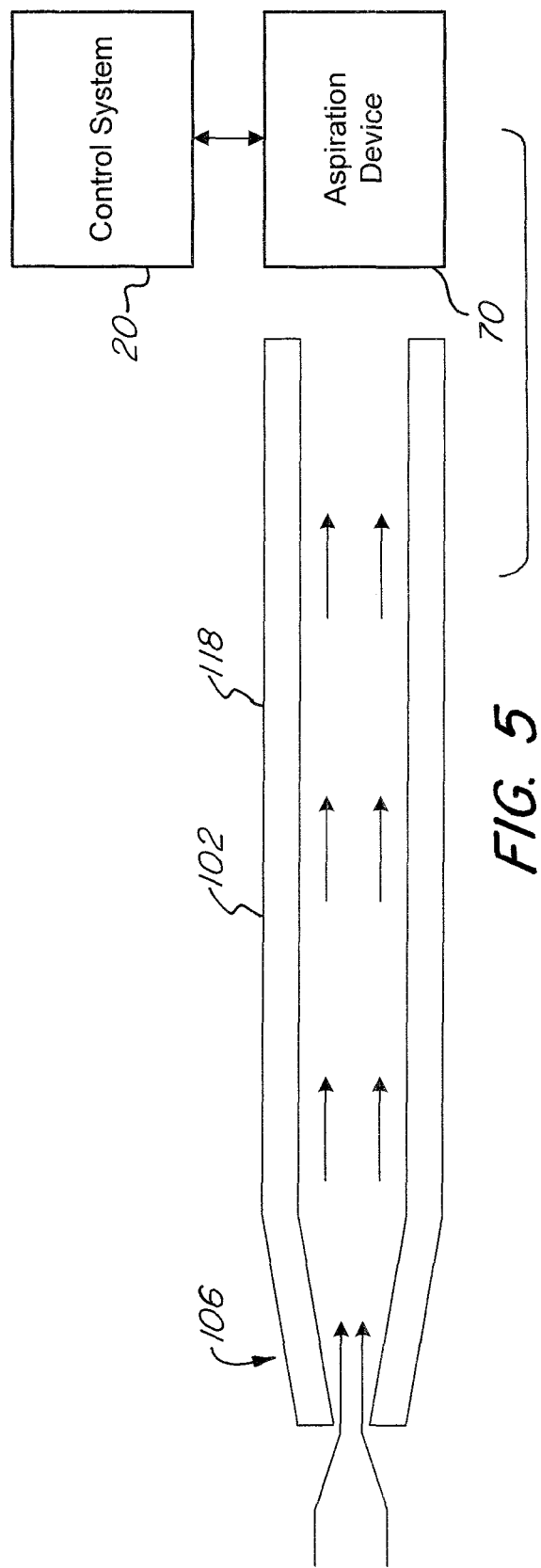
FIG. 4
FIG. 5

BODY CAVITY DILATION SYSTEM

FIELD OF THE INVENTION

The invention relates to a system and method for dilation of a body cavity, and more particularly, a system and method for the insertion of a series of members each having a progressively larger diameter into a body cavity to distend the cavity for insertion of a medical device or tool.

BACKGROUND OF THE INVENTION

The removal of unwanted and/or life threatening biological material from interior portions of bodily cavities, such as organs, vessels, articular joints and structures, sinuses, and various bodily lumens, is a common medical procedure in various medical specialties and disciplines, such as pulmonology, cardiology, urology, gynecology, gastro-enterology, neurology, otolaryngology, orthopedics, and general surgery. Accordingly, various instruments and methods have been employed to perform these procedures.

In one example, the nasal cavity (or nasal fossa) is a large air-filled space above and behind the nose in the middle of the face. The floor of the nasal cavity, which forms the roof of the mouth, is made up by the bones of the hard palate: the horizontal plate of the palatine bone posteriorly and the palatine process of the maxilla anteriorly. To the front of the nasal cavity is the nose, while the back blends, via the choanae, into the nasopharynx.

The paranasal sinuses are hollow cavities in the skull connected by small openings, known as ostia, to the nasal canal. Each ostium between a paranasal sinus and the nasal cavity is formed by bone covered by a layer of mucosal tissue. Normally, air passes into and out of the paranasal sinuses through the ostia and into the nasal canal.

The paranasal sinuses include the maxillary sinuses, the frontal sinuses, the ethmoid sinuses, and the sphenoid sinuses. The maxillary sinuses are also called the maxillary antra and are the largest of the paranasal sinuses. They are located under the eyes, in the maxillary bones. The frontal sinuses are superior to the eyes, in the frontal bone, which forms the hard part of the forehead. The ethmoid sinuses are formed from several discrete air cells within the ethmoid bone between the nose and the eyes. The sphenoid sinuses are in the sphenoid bone at the center of the skull base under the pituitary gland. Sinusitis is an inflammation of the sinus lining commonly caused by bacterial, viral and/or microbial infections; as well as, structural issues such as ostial blockage. Symptoms include nasal congestion, facial discomfort, nasal discharge, headache, and fatigue.

37 million people suffer from chronic sinusitis in the US alone. Initial medical therapy, amounting to $8 B per year, consists of antibiotics, decongestants, and steroids. 25% of patients do not respond to medical therapy. Functional Endoscopic Sinus Surgery (FESS) utilizes debriding equipment to enlarge sinus ostia to encourage drainage. 330,000 FESS are performed/year with an 80% success rate at 3 years. However, complications include CSF leaks, blindness, synechieae, alteration in bone growth, bleeding and infection. FESS is not 100% effective and has a known revision rate of 10%.

More recently, the use of balloon catheters in sinus surgery have been used as described in U.S. Pat. No. 7,854,744 to Becker. In at least some procedures where it is desired to position a balloon catheter in the ostium, it is necessary to advance the catheter through complicated or tortuous anatomy in order to properly position the balloon within the desired sinus ostium. Also, there is a degree of variation in the intranasal and paranasal anatomy of human beings, thus making it difficult to use the stiff-shaft pre-shaped balloon catheters of Becker for use in all individuals. The Becker patent describes the necessity of having available a set of balloon catheters, each having a particular fixed angle so that the physician can select the appropriate catheter for the patient's anatomy.

A series of U.S. patents to Chang et al. (e.g. U.S. Pat. No. 7,727,226) disclose methods utilizing flexible balloon catheter devices for use in ENT procedures. A sizing balloon situated around the dilating balloon may be inflated using an inflating medium, such as saline with radio-opaque contrast agent or carbon dioxide gas. The distal region of the sizing balloon is supposed to enable the operator to estimate the size of the anatomical opening or the diameter of the narrowest region in a tubular anatomical region.

A common but often undesirable effect resulting from the above described methods and apparatus, is the possibility of the inflation of the balloon portion of the catheter causing sinus ostial fracture, which is sometimes an intended part of the procedure.

Hence, there is a significant need for systems and methods for deforming a body cavity, which in one example, may comprise the sinus ostia, that will not suffer from the drawbacks described herein while still being relatively simple to use and accommodates a single-use strategy.

While the sinus ostia has been described herein, the over inflation of balloon type catheters used in connection with numerous different types of medical procedures and the associated possible breaking or tearing of the cavity due to the inflation is a significant problem.

SUMMARY OF THE INVENTION

What is desired then is a device and method for deforming a body cavity that allows the cavity to deform without fracture.

It is further desired to provide a device and method for removing biological matter from the body cavity without fracturing the cavity.

It is still further desired to provide a device and method for delivering diagnostic and/or therapeutic agents to body cavity without fracturing the cavity.

It is also desired to provide a device and method for dilating a body cavity and a safe and efficient manner.

The device may include a series of members (e.g., three or four) of increasing outer diameter (OD). In one example, the OD's may be approximately 3 mm, 4.5 mm, 6 mm and 9 mm. Each member may be provided with a flexible distal end with a tapered tip for sliding into the cavity, which in one example may comprise the sinus ostia. A first member, comprising the smallest OD, is initially inserted to dilate the cavity. Subsequently, a second member, having an OD larger than the first member, is advanced over the first member to further dilate the cavity. Finally, a third member, having an OD larger than the second member, is advanced over the second member to dilate the cavity so that a medical device or tool may then be inserted into the cavity. While only three members are described here, it is contemplated that any number of additional members may be subsequently advanced to dilate the cavity as desired.

In one example, the first member is provided with a relatively large handle at a proximal end to steer the first member through the cavity (ostia) for initial impaction and possible dilation. Each subsequent member may be provided with a small flanged handle at a proximal end thereof for pushing in or pulling out the relevant member. Each subsequent member may also be provided with a set of "guard wires" running along an outside of the respective member.

The guard wires attached to each respective member, may be secured to a guard wire mount located near the proximal end of each subsequent member, and the distal, ball shaped ends are designed to contact the outer edge of a patient (e.g., a patient's nose when used to dilate the sinus ostia) so as to prevent the relevant member from being advanced too far into the cavity causing potential damage to the cavity. It is contemplated that proximal ends of the guard wires may be provided with multiple balls for securing the guard wires to the guard wire mount. In this manner, the length of the wires, which corresponds to the distance that the subsequent member may be advanced into the cavity, may be adjusted by the physician.

Once subsequent members (e.g., those with a larger OD) have been advanced into the cavity, the previous member(s) may be withdrawn. In one example, the guard wires comprise a plastic material, which may be cut when a previous member is ready to be withdrawn, since the guard wire mount may be attached to the previous member.

It is still further contemplated that a relatively small diameter image guide, (e.g., an optical fiber) and a light guide may be advanced through the first member for visualization. Once a larger diameter member, such as, for example, a third member with 6 mm OD has been inserted; the smaller diameter members may be removed, and a larger diameter, such as, for example, a 3 mm or 4 mm camera, may be inserted for higher resolution imaging. Such cameras, catheters, and/or therapeutic agents may be introduced into the first member via one or more ports located at the proximal end of the handle.

Incorporating image guidance into the design of an articulating dilation system will enable physicians to quickly navigate to, accurately identify and appropriately dilate the anatomy to open the body cavity and deliver irrigation and therapeutic solutions.

For this application the following terms and definitions shall apply:

The term "network" as used herein includes both networks and internetworks of all kinds, including the Internet, and is not limited to any particular network or inter-network.

The terms "first" and "second" are used to distinguish one element, set, data, object or thing from another, and are not used to designate relative position or arrangement in time.

The terms "coupled", "coupled to", "coupled with", "connected", "connected to", and "connected with" as used herein each mean a relationship between or among two or more devices, apparatus, files, programs, applications, media, components, networks, systems, subsystems, and/or means, constituting any one or more of (a) a connection, whether direct or through one or more other devices, apparatus, files, programs, applications, media, components, networks, systems, subsystems, or means, (b) a communications relationship, whether direct or through one or more other devices, apparatus, files, programs, applications, media, components, networks, systems, subsystems, or means, and/or (c) a functional relationship in which the operation of any one or more devices, apparatus, files, programs, applications, media, components, networks, systems, subsystems, or means depends, in whole or in part, on the operation of any one or more others thereof.

The terms "process" and "processing" as used herein each mean an action or a series of actions including, for example, but not limited to, the continuous or non-continuous, synchronous or asynchronous, routing of data, modification of data, formatting and/or conversion of data, tagging or annotation of data, measurement, comparison and/or review of data, and may or may not comprise a program.

In one example, a device for dilating a body cavity is provided comprising a first member including: a first elongated body portion with a first proximal end and a first distal end defining a first length, the first distal end being deflectable, the first elongated body portion defining a first outside diameter (OD) and having a first channel therein extending from the first proximal end to the first distal end, the first channel defining a first inside diameter (ID) and a handle coupled to the first proximal end, the handle including a deflection control for deflection of the first distal end. The device further comprises a second member including: a second elongated body portion with a second proximal end and a second distal end defining a second length, the second distal end being deflectable, the second elongated body portion defining a second OD and having a second channel therein extending from the second proximal end to the second distal end, the second channel defining a second ID. The device is provided such that the second ID being larger than the first OD such that the first member is longitudinally moveable within of the second channel. The device further comprises a third member including: a third elongated body portion with a third proximal end and a third distal end defining a third length, the third distal end being deflectable, the third elongated body portion defining a third OD and having a third channel therein extending from the third proximal end to the third distal end, the third channel defining a third ID. The device is provided such that the third ID is larger than the second OD such that the second member is longitudinally moveable within of the third channel.

In another example, a device for dilating a body cavity is provided comprising a first member including: a first elongated body portion with a first proximal end and a first distal end defining a first length, the elongated body portion defining a first outside diameter (OD) and having a first channel therein extending from the first proximal end to the first distal end, the first channel defining a first inside diameter (ID), and a handle coupled to the first proximal end. The device further comprises a second member including: a second elongated body portion with a second proximal end and a second distal end defining a second length, the second elongated body portion defining a second OD and having a second channel therein extending from the second proximal end to the second distal end, the second channel defining a second ID. The device is provided such that the second ID being larger than the first OD such that the first member is longitudinally moveable within of the second channel. The device still further comprises a wireless energy generator coupled to the first or second channel such that wireless energy is transmitted through the respective first or second channels.

Other objects of the invention and its particular features and advantages will become more apparent from consideration of the following drawings and accompanying detailed description.

BRIEF DESCRIPTION OF THE DRAWINGS

FIGS. 4-6 are diagrams of the device according to FIG. 3.

DETAILED DESCRIPTION OF THE INVENTION

Figure 1:
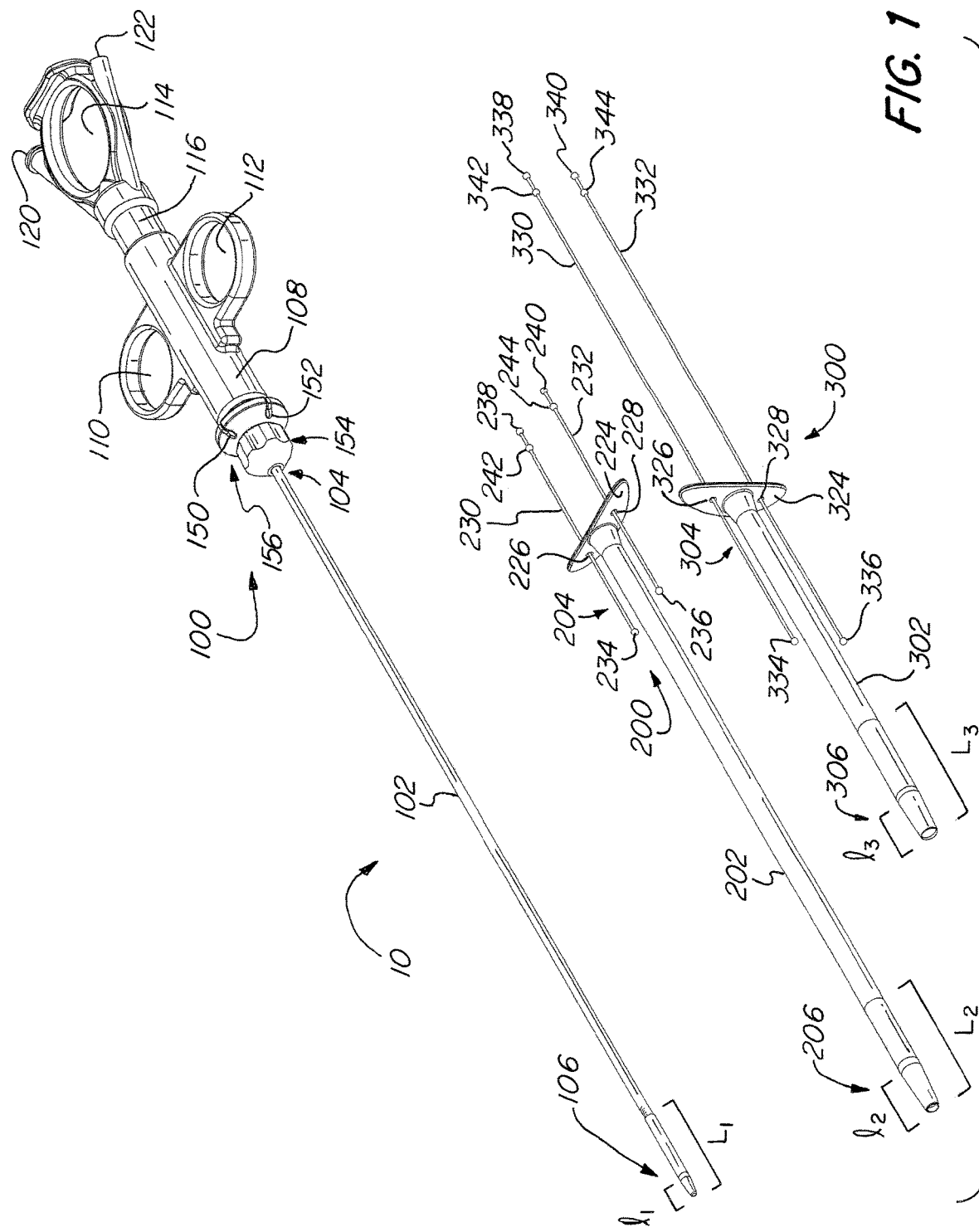
FIG. 1 is a perspective view of a device according to the invention in an unassembled condition.

Referring now to the drawings, wherein like reference numerals designate corresponding structure throughout the views.

FIG. 1 depicts a device 10 for dilating a body cavity shown in an unassembled condition. The device 10 generally comprises a first member 100, a second member 200, and a third member 300 all of which are attachable to each other to form the assembled device 10 as shown in FIG. 2.

Figure 2:
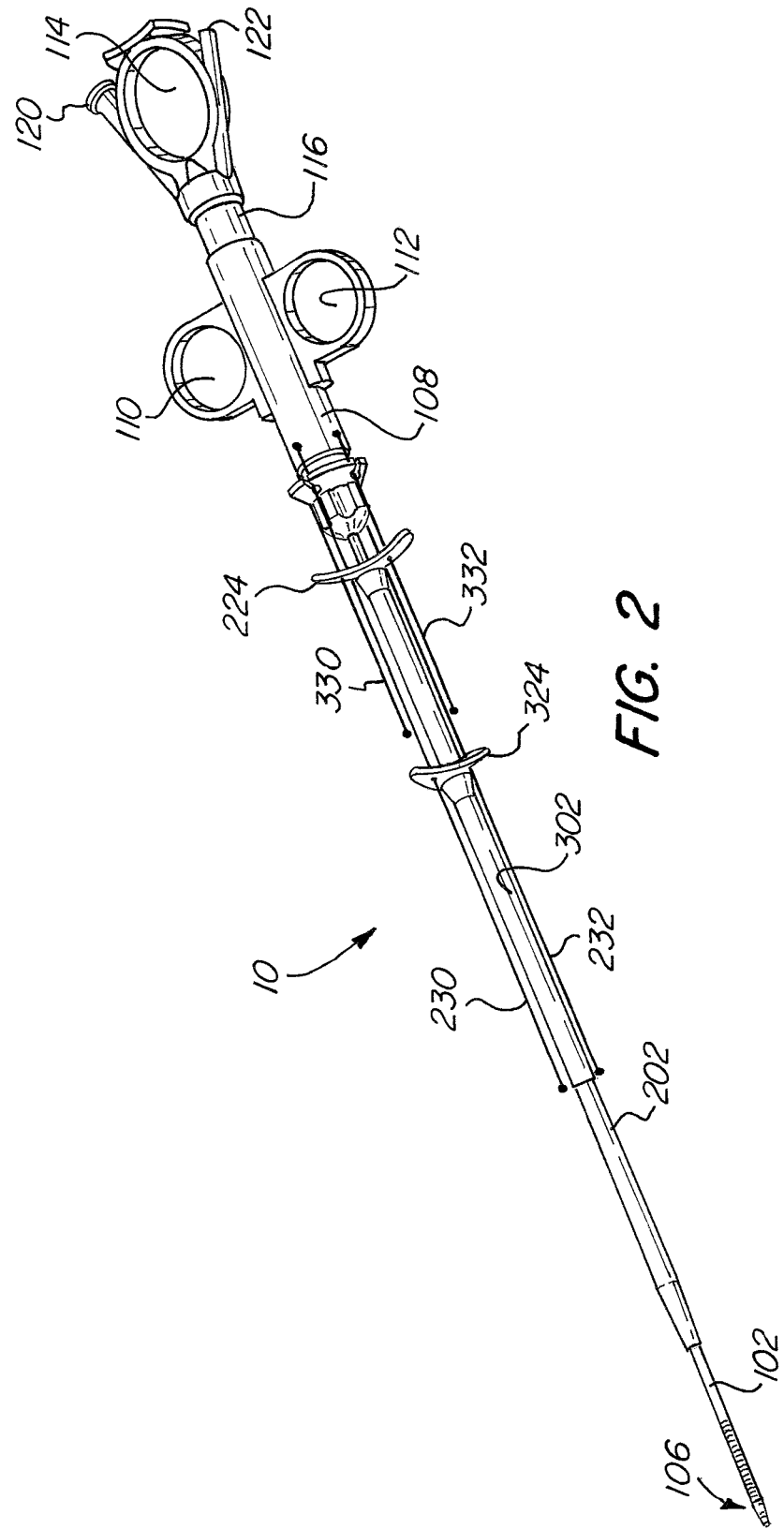
FIG. 2 is a perspective view of the device of FIG. 1 in an assembled condition.

In particular, the second member 200 is configured to be able to slide over the first member 100, and the third member 300 is configured to be able to slide over the second member 300 (FIG. 2).

The first member 100 comprises a first elongated body portion 102 having a proximal end 104 and distal end 106. Affixed to the proximal end 104 is a handle 108, which is designed to be gripped by a user during use. The handle 108 is provided with finger holes 110, 112 and an opening 114 for the user's thumb. The handle is provided with a plunger 116 that may be depressed linearly into the handle 108 to actuate deflection of the distal end 104 of the first elongated body portion 102. The amount of deflection will be proportional to the amount the plunger 116 is displaced linearly. In this manner, the user may grip the first member 100 securely while actuating the device.

Figure 7:
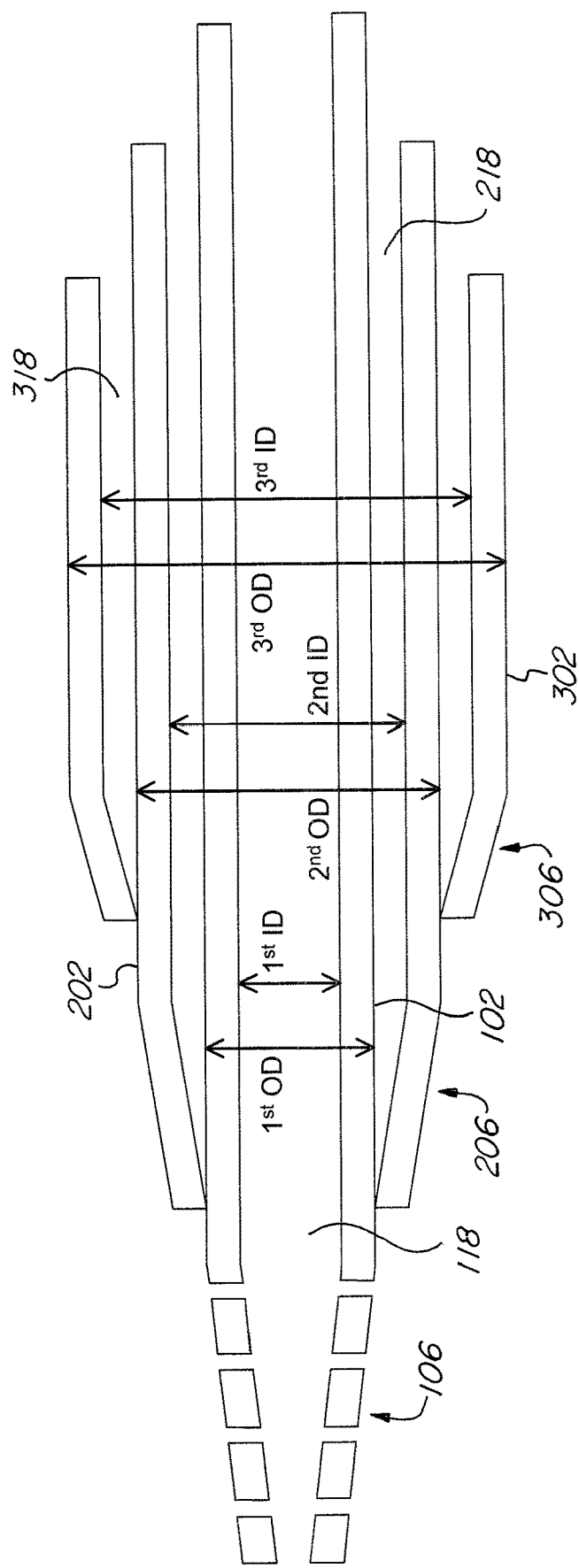
FIGS. 7-12 are diagrams of the device according to FIG. 2.

The first elongated body portion 102 is provided with a first channel 118 that is defined by a first inside diameter (ID) as is illustrated in FIG. 7. The outer perimeter of the first elongated body portion 102 is defined by a first outer diameter (OD). It is contemplated that in one example, the first elongated body portion 102 may be provided to articulate up to 120° from its distal tip throughout the length of its construct and dimensionally taper over a 20.0 mm distance ($L_1$) from a distal diameter of 1.5 mm to a proximal diameter of 3.5 mm and have a taper length ($l_1$) comprising 7 mm. The first channel 118 may have an I.D=1.25 mm, while the first elongated body portion 102 may have an O.D=2.9 mm. The distal end 106 of first elongated body portion 102 is shown with openings (fenestrations) provided therein, which may comprise openings that are positioned at various radial and axial displaced positions around the distal end 106. While only the distal end 106 is illustrated comprising the fenestrations, it is contemplated that the fenestration may be provided anywhere along a longitudinal length of first elongated body portion 102. Likewise, fenestrations may be provided on any of the members 100, 200, 300.

The second member 200 comprises a second elongated body portion 202 having a proximal end 204 and distal end 206. The second elongated body portion 202 is provided with a second channel 218 that is defined by a second ID as is illustrated in FIG. 7. The outer perimeter of the second elongated body portion 202 is defined by a second OD.

It is contemplated that in one example, the second elongated body portion 202 may be provided to articulate up to 120° from its distal tip throughout the length of its construct and dimensionally taper over a 25.0 mm distance ($L_2$) from a distal diameter of 3.3 mm to a proximal diameter of 4.5 mm and have a taper length ($l_2$) comprising 10 mm. The second channel 218 may have an I.D=3.2 mm, while the second elongated body portion 202 may have an O.D=4.5 mm.

The third member 300 comprises a third elongated body portion 302 having a proximal end 304 and distal end 306. The third elongated body portion 302 is provided with a third channel 318 that is defined by a third ID as is illustrated in FIG. 7. The outer perimeter of the third elongated body portion 302 is defined by a third OD.

It is further contemplated that in another example, the third elongated body portion 302 may be provided to articulate up to 120° from its distal tip throughout the length of its construct and dimensionally taper over a 35.0 mm distance ($L_3$) from a distal diameter of 5.65 mm to a proximal diameter of 6.5 mm and have a taper length ($l_3$) comprising 12.5 mm. The third channel 318 may have an I.D=4.7 mm, while the third elongated body portion 302 may have an O.D=6.5 mm.

The central cannulations within the disparate articulating members will enable transmission of various sized guide wires, imaging systems, diagnostic and therapeutic devices and pharmacologics through their central channels (118, 218, 318). The proximal articulating members will advance over the distal most articulating members to sequentially enlarge the diameter of the intended cavity. As a proximal member is wedged into place over a smaller distal member, the distal member of the construct may be removed from its distal insertion point through the center of the proximal construct and removed from the back of the hand piece; effectively creating a larger central channel through which larger imaging systems and therapeutic devices may be delivered to the intended anatomy through the proximal member.

The handle 108 will facilitate insertion, steering and articulation of the distal articulating members. The handle 108 may also include a mechanism to release a distal member from its distal insertion point and from its locking association with its corresponding proximal member. The hand piece will include a removal mechanism to retrieve a distal member(s) from its insertion point and pull it through the central channel of the construct to be removed proximally. The inclusion of a 'palm' grip for handle 108 is provided to facilitate the application of linear force upon the distal members to promote their insertion.

While only three members (100, 200, 300) are illustrated in FIGS. 1 and 2, it is contemplated that a fourth member could be provided and fitted over the third member 300.

For example, the fourth member could be provided to articulate up to 120° from its distal tip throughout the length of its construct and dimensionally taper over a 50 mm distance from a distal diameter of 6.7 mm to a proximal diameter of 9 mm and have a taper length comprising 15.0 mm. A fourth channel may be provided therein having an I.D=6.7 mm, while a fourth elongated body portion may have an O.D=9.0 mm.

The articulating section of each member then, may be provided to articulate up to 120° from its distal tip throughout the length of its construct. The overall length of the shaft section(s) of the device may be 200 mm fully extended and 150 mm telescopically reduced. The shaft may further include identifying marker bands upon its substrate that illustrate dimensional metrics to communicate the depth of insertion of the various member sections. The shaft may further include identifying marks that communicate the direction of the articulation of the member(s) being deployed.

Also illustrated in FIGS. 1 and 2 are ports 120, 122, which in this example, extend from the plunger 116 beyond opening 114. The ports are in communication with channels in the handle 108 for connection to various equipment, including, for example, irrigation equipment, aspiration equipment, drug delivery equipment, wireless energy generation equipment and so on. Ports 120, 122 may be in communication with first channel 118 such that, for example, irrigation equipment may be connected to port 120 and aspiration equipment may be connected to port 122. The various equipment could then be sequentially actuated to provide irrigation and aspiration to the body cavity. Additionally, port 120 could be connected to drug delivery equipment such that an anaesthetizing drug may be administered to the body cavity prior to the body cavity being dilated and a surgical procedure being performed. Once the anaesthetizing drug has been administered, the drug delivery equipment could be removed and irrigation equipment could be attached for the procedure. Additionally or alternatively, an ultrasonic generator could be attached to port 120 to provide ultrasonic energy to break up mucus that may be obstructing the sinus ostia, which could then be extracted via an aspiration device. In any event, it is contemplated that various different types of device may be coupled to ports 120, 122 depending on the procedure to be performed, and connection of the devices may be facilitated by a mechanical connection that allows for quick and easy detaching and attaching of various lines.

Any of various agents useful in therapeutic application can be delivered in the above described manner. For example, the device 10 may be used to deliver any number of things to assist with opening the cavity, circulation, aspiration, respiration, assisting the decomposition of an obstruction, or stimulating healing in the affected area, including air, aspirates, drugs, biologics, biogenetic agents, nano-particulates, solutions, stem cell and gene therapies, and stents and scaffolds. Examples of diagnostic or therapeutic agents are contrast agents, a pharmaceutically acceptable salt or dosage form of an antimicrobial agent (e.g., antibiotic, antiviral, anti-parasitic, antifungal, etc.), an anesthetic agent, an analgesic agent, a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, or immunomodulator), an allergen or another substance that causes secretion of mucous by tissues, anti-proliferative agents, hemostatic agents to stop bleeding, cytotoxic agents (e.g. alcohol), biological agents such as protein molecules, stem cells, genes or gene therapy preparations etc.

Antimicrobial agents can include, but are not limited to, acyclovir, amantadine, amikacin, gentamicin, tobramycin, amoxicillin, amphotericin B, ampicillin, sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clavulanate, clotrimazole, ciprofloxacin, clarithromycin, clindamycin, dapsone, dicloxacillin, doxycycline, erythromycin, fluconazole, foscarnet, ganciclovir, atifloxacin, imipenem, cilastatin, isoniazid, itraconazole, ketoconazole, metronidazole, nafcillin, nystatin, penicillin, penicillin G, pentamidine, piperacillin, rifampin, quinupristin-dalfopristin, ticarcillin, trimethoprim, sulfamethoxazole, tazobactam, valacyclovir, vancomycin, mafenide, silver sulfadiazine, mupirocin, nystatin, triamcinolone, butoconazole, miconazole, tioconazole, and combinations thereof. Anti-inflammatory agents can include, but are not limited to, beclomethasone, flunisolide, fluticasone proprionate, triamcinolone acetonide, budesonide, loterednol etabonate, mometasone, aclometasone, desonide, hydrocortisone, betamethasone, clocortolone, desoximetasone, fluocinolone, flurandrenolide, prednicarbate, amcinonide, desoximetasone, diflorasone, fluocinolone, fluocinonide, halcinonide, clobetasol, salicylic acid derivatives, aspirin, sodium salicylate, choline magnesium trisalicylate, salsalate, diflunisal, sulfasalazine, olsalazine, acetaminophen, indomethacin, sulindac, tolmetin, dicofenac, ketorolac, ibuprofen, naproxen, flurbiprofen, ketoprofen, fenoprofen, oxaprozin, mefenamic acid, meloxicam, piroxicam, meloxicam, nabumetone, rofecoxib, celecoxib, etodolac, nimesulide and combinations thereof.

Exemplary decongestants include, but are not limited to, pseudoephedrine, xylometazoline, oxymetazoline, phenylephrine, epinephrine, and combinations thereof.

In some examples, the agent comprises an anesthetic agent. The anesthetic agent is delivered to nasal passages in the manner described above to provide local pain relief such that further surgical procedures may be performed on the passages, such as, for example, dilation of the sinus ostia passage. Any desirable anesthetic agent may be delivered by the method of the present invention. Some examples include, but are not limited to, cocaine, lidocaine, tetracaine, and combinations thereof.

In additional examples, the device 10 is used to deliver a mucolytic agent. As described above, when a patient has a sinusitis condition, the mucosal tissue in the nasal passages becomes inflamed, which causes accumulation of mucus in the passageways, thereby blocking them. Mucolytic agents are designed to help loosen and clear the mucus from the nasal passages by breaking up the sputum to facilitate removal of the blockages in the passageways. Such mucolytic agents include, but are not limited to, cromolyn, nedocromil, azelastine, diphenhydramine, loratidine, acetylcysteine, bromheksin, guiafenesin, and combinations thereof. The mucolytic agents are delivered to the nasal passages by the balloon catheter system to help loosen the mucus such that it can be more easily drained or flushed from the passages to relieve the sinusitis condition.

In further examples, the device 10 delivers an antihistamine agent. The antihistamine agents, or histamine antagonists, help to prevent many of the symptoms of an allergic reaction in the nose (i.e. rhinitis), such as itching, runny nose and sneezing. The antihistamines work by blocking histamine attachment to histamine receptors in the brain, which prevents increased vascular permeability that leads to runny nose. Any type of antihistamine agents may be delivered by the method of the present invention, including but not limited to, acrivastine, azelastine, bilastine, brompheniramine, buclizine, bromodiphenhydramine, carbinoxamine, cetirizine, cyclizine, chlorpheniramine, chlorodiphenydramine, clemastine, cromolyn, cyproheptadine, desloratadine, dexbrompheniramine, dexchlorpheniramine, dimenhydrinate, dimetindene, diphenhydramin, doxylamine, ebastine, embramine, fexofenadine, hydroxyzine, levocetirizine, loratadine, nedocromil, olopatadine, phenindamine, pheniramine, phenyltoloxamine, promethazine, pyrilamine, rupatadine, tripelennamine, triprolidine, and combinations thereof.

In yet further examples, the device 10 delivers an osteolytic agent. The osteolytic agents cause breakdown of bone tissue in the body or osteolysis. This can occur, for example, by removal of calcium from the bone tissue, which causes dissolution of the bone. As described above, in patients suffering from a chronic or recurring sinusitis, it is desirable to enlarge the sinus ostia passages and remove obstructions in these passages to relieve the symptoms of sinusitis. In order to do that, some surgical procedures involve breakage or resection of the bone tissue. The delivery of osteolytic agents to the nasal passages facilitates removal of the bone tissue.

An exemplary anti-cholinergic is ipratropium bromide.

Diuretics can include, but are not limited to, furosemide and/or hyperosmolar agents such as sodium chloride gel or other salt preparations.

Referring again to FIGS. 1 and 2, second member 200 is provided with a flange 224, while third member 300 is provided with a flange 324. Each of flange 224, 324 are provided with penetrations 226, 228, 326, 328, which allow the passage of guard wires 230, 232, 330, 332 respectively.

The guard wires 230, 232, 330, 332 are each provided with spherical distal ends 234, 236, 334, 336 respectively. Likewise, guard wires 230, 232, 330, 332 are each provided with spherical proximal ends 238, 240, 338, 340. Additional spherical objects 242, 244, 342, 344 are provided linearly displaced along a length of each of guard wires 230, 232, 330, 332 forming a space between each sphere on the proximal end that is designed to fit into a respective cavity 150, 152, 154, 156 provided radially around the handle 108 at 90 degree intervals with respect to each other, to secure the guard wires 230, 232, 330, 332 with respect to the handle 108. FIG. 2 illustrates the guard wires 230, 232, 330, 332 coupled to each respective cavity 150, 152, 154, 156.

It can also be see that the flange 226 is provided with two tab portions that each extend at approximately 90 and 270 degrees and include penetrations 226, 228 that correspond with cavities 152, 156; while flange 326 includes two tabs portions that each extend at approximately 0 and 180 degrees, and include penetrations 326, 328 that correspond with cavities 150, 154.

In the example where four members are provided, the handle will be provided with six cavities where each of the three members that would extend over the first members are provided with flanges and would include tab portions that would be formed at 60 degree intervals for securing six guard wires to the handle 108.

The guard wires 230, 232, 330, 332 may be formed of a stiff plastic material and are provided to provide a visual feedback to the physician as to the safe insertion distance of the members into the body cavity. For example, the first member 100 is of a relatively small diameter and should therefore not pose a substantial risk to the patient when inserted into the body cavity for drug delivery, initial visualization and initial treatment. However, when the second member 200 is advanced over the outside of the first member 100, the physician will want to be careful not to advance the larger diameter member too far into the nasal cavity. The guard wires 230, 232 will come into contact with the patient's face when the second member has been fully advanced into the body cavity indicating that the member should not be advanced any further. Likewise, the guard wires 330, 332 provide a similar function with respect to the third member 300. It is also contemplated that exterior surfaces of the elongated body portions 102, 202, 302 may be provided with clearly visible length indications providing the physician with an exact indication of how far the respective elongated body portion has been advanced into the body cavity.

Figure 3:
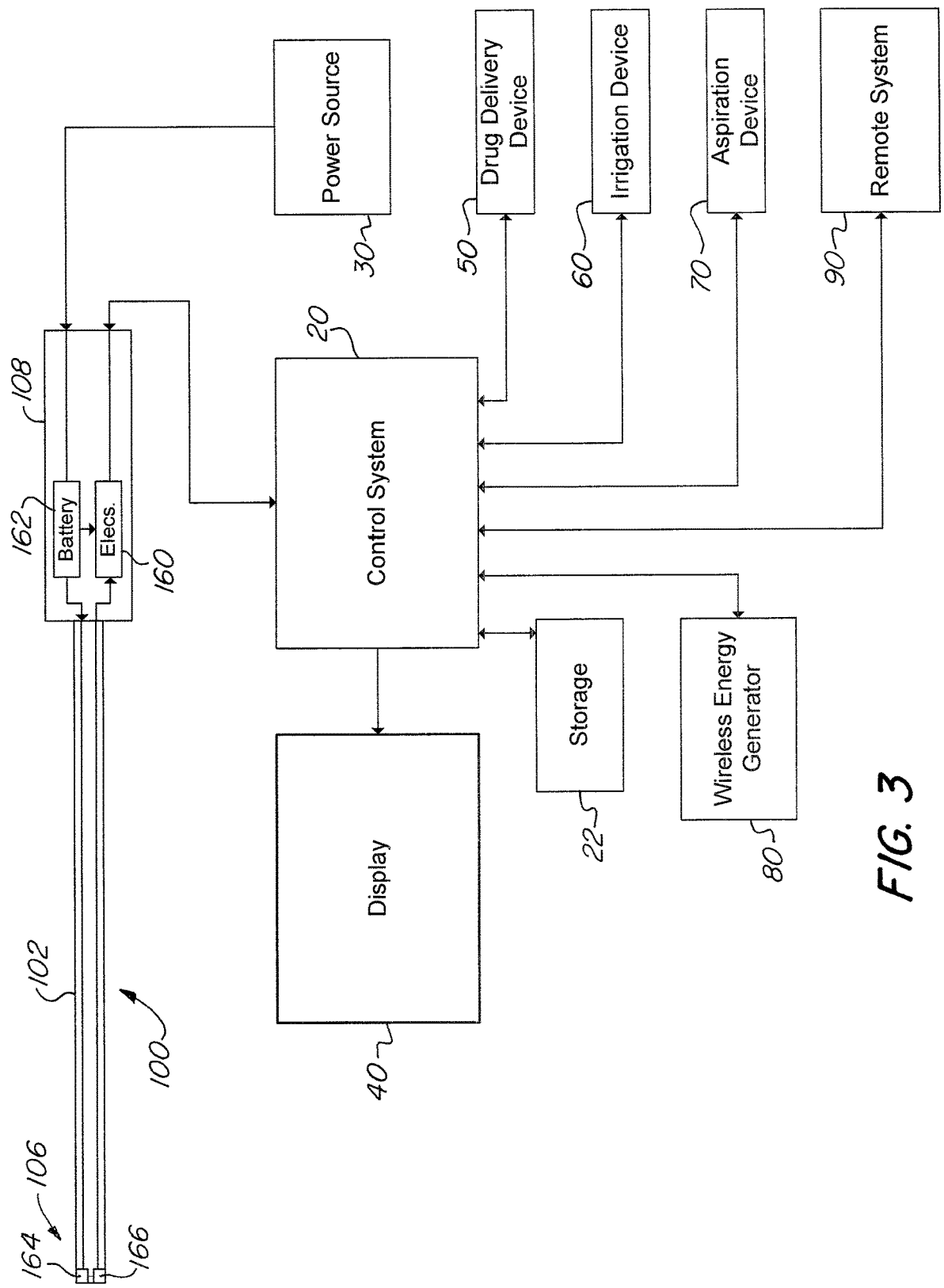
FIG. 3 is a block diagram of the device according to FIG. 1 illustrating the associated system.

Turning now to FIG. 3, the first member 100 is illustrated coupled to a control system 20, which may comprise a computer. While not illustrated, various input devices may be used for a user to input information to control system 20 including, for example, a keyboard, a mouse, a touch screen, etc. The first member 100 includes electronics 160 and battery 162, both of which are positioned in handle 108. Also shown is power source 30, which is shown connected to battery 162. It should be understood that while lines with arrows are shown in FIG. 3, the figure is a functional block diagram to illustrate the functioning of the system and should not be construed as limiting the system to a "wired" configuration. For example, the power source 30 may comprise a "wired" solution comprising a charger that may be plugged into a standard 120V outlet; or may comprise a wireless power charging solution. Likewise, the double arrow line connecting electronics 160 with control system 20 is provided to illustrate that the control system 20 communicates with the electronics 160, which communication may be "wired" or wireless.

A light source 164 and an imaging device 166 are illustrated at the distal end 106 of first elongated member 102. The light source 164 is coupled to and receives power from battery 162. Likewise, imaging device 166 is coupled to and receives power from battery 162. Imaging device 166 may comprise virtually any type of device suitable for generating illuminating light and may comprise, for example, a light emitting diode (LED).

Imaging device 166 is illustrated as coupled to electronics 160 and is provided to generate image data corresponding to light reflected from the area ahead of the distal end 106. The image data is transmitted to electronics 160, which then processes and transmits the image data to control system 20. Connected to control system 20 is display 40, which may comprise any type of screen for displaying the image data, including, for example, an LCD display, a touch screen, etc.

Also connected to control system 20 is storage 22, drug delivery device 50, irrigation device 60, aspiration device 70, wireless energy generator 80 and remote system 90. The storage 20 may comprise any type of data storage device including an internal hard drive to control system 20, internal memory, an external hard drive (pluggable), a USB (thumb) drive, an optical drive and the like. Likewise, the remote system 90 may comprise a computer coupled to control system 20 via a network connection for control and/or connection to control system 20. For example, the remote system 90 may be a passive system limited to receiving data, such as the image data for offsite storage and display (e.g., in a class room for instructional purposes) and so on. Alternatively, the remote system 90 may comprise an active system allowing a remote user to take actions during the procedure. For example, a remote user (surgeon) may be watching the surgical procedure remotely and decide that a still picture or a video clip of a specified length should be saved of the procedure. The remote user could then enter a command to this effect via the remote system 90, which in turn would pass the command to the control system 20 to save the video clip or the still image on storage 22. This is provided as just a few examples of how the remote system 90 could interact with control system 20

Drug delivery device 50 is shown coupled to control system 20 indicating that the control of the drug delivery device 50 may occur via control system 20. A conduit or pipe would be connected from drug delivery device 50 to the first member 100 providing a pathway for the drug to be transmitted to the first channel 118 for introduction into the body (FIG. 4).

Likewise, irrigation device 60 and aspiration device 70 (FIGS. 4 & 5) are shown connected to control system 20 indicating that control of these devices may be handled by the control system. Arrows between irrigation device 60, aspiration device 70 and control system 20 indicate that control system 20 provides commands to the various devices and receives data from the connected devices (e.g., settings data, confirmation that commands were carried out, flow data, etc.).

Figure 6:
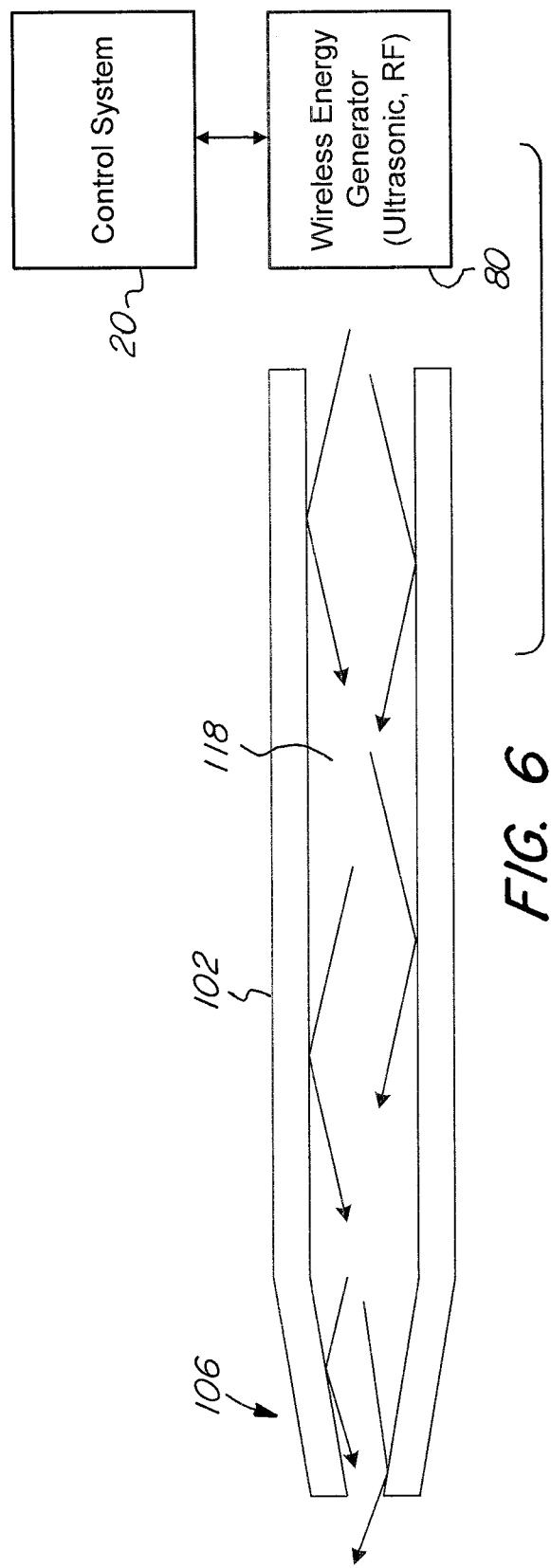

Wireless energy generator 80 may comprise any type of device that may be used to generated wireless energy that may be transmitted to the body cavity, including, for example, RF and ultrasonic energy (FIG. 6). It is contemplated that the wireless energy may be transmitted to a body cavity to perform a surgical procedure. In one example, ultrasonic energy may be used to break up mucus in the sinus ostia and so on. The wireless energy generator 80 receives commands from and transmits data to control system 20. It is further conceived that the fenestrations may function to amplify and/or communicate the acoustic pressure and/or intensity to the surrounding anatomy.

Figure 8:
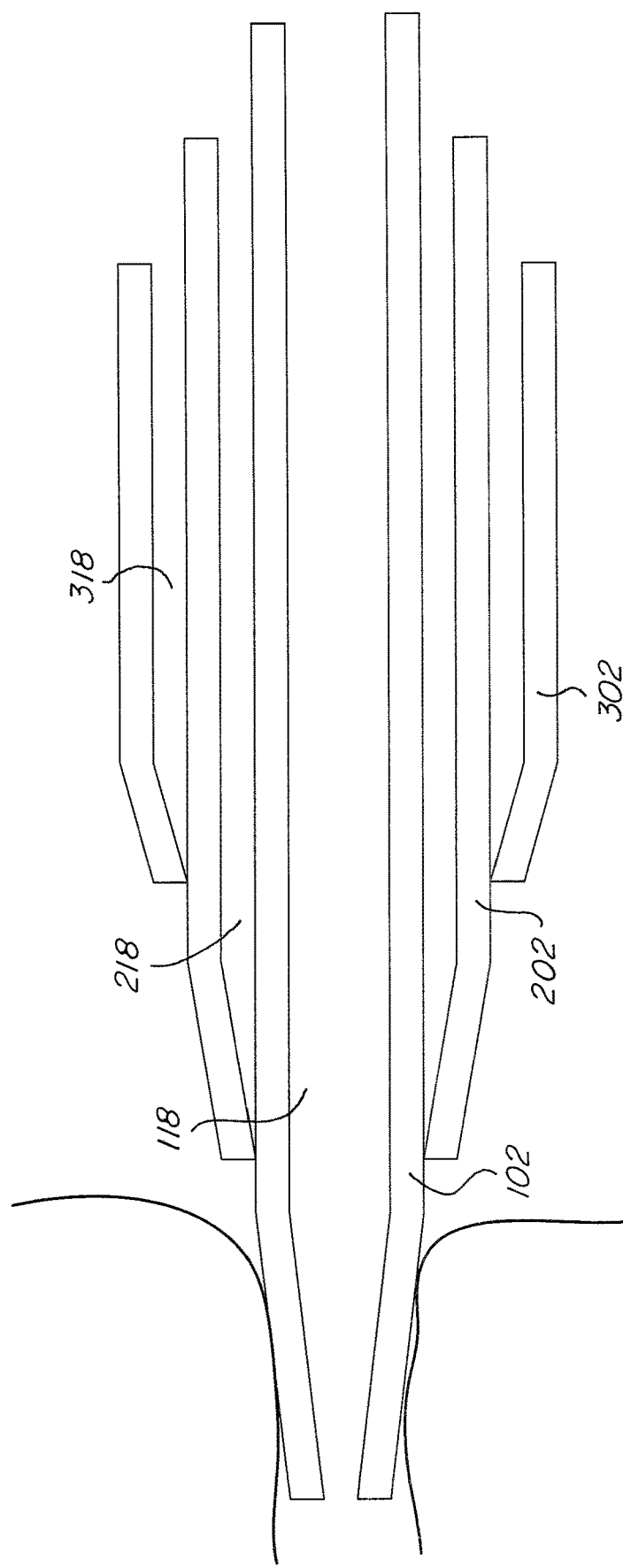

FIGS. 8-12 illustrate one example of how the device may be utilized to dilate a body cavity. FIG. 8 illustrates advancement of the device into a body cavity with the first member 100 being introduced. During the introduction of the first member 100, any of the previously discussed procedures may occur, including, drug delivery, visualization, introduction of wireless energy, irrigation, aspiration and so on.

Figure 9:
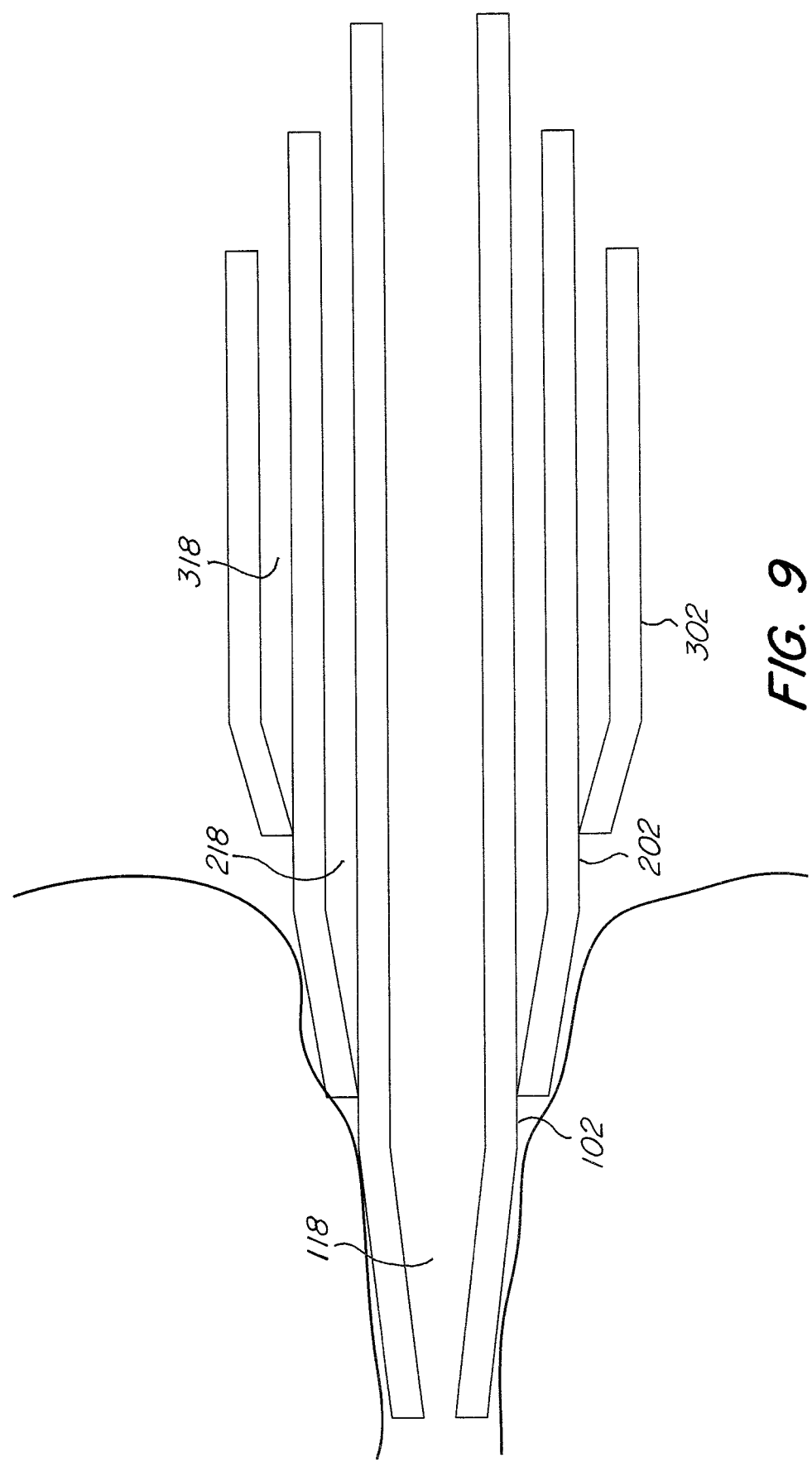
Figure 10:
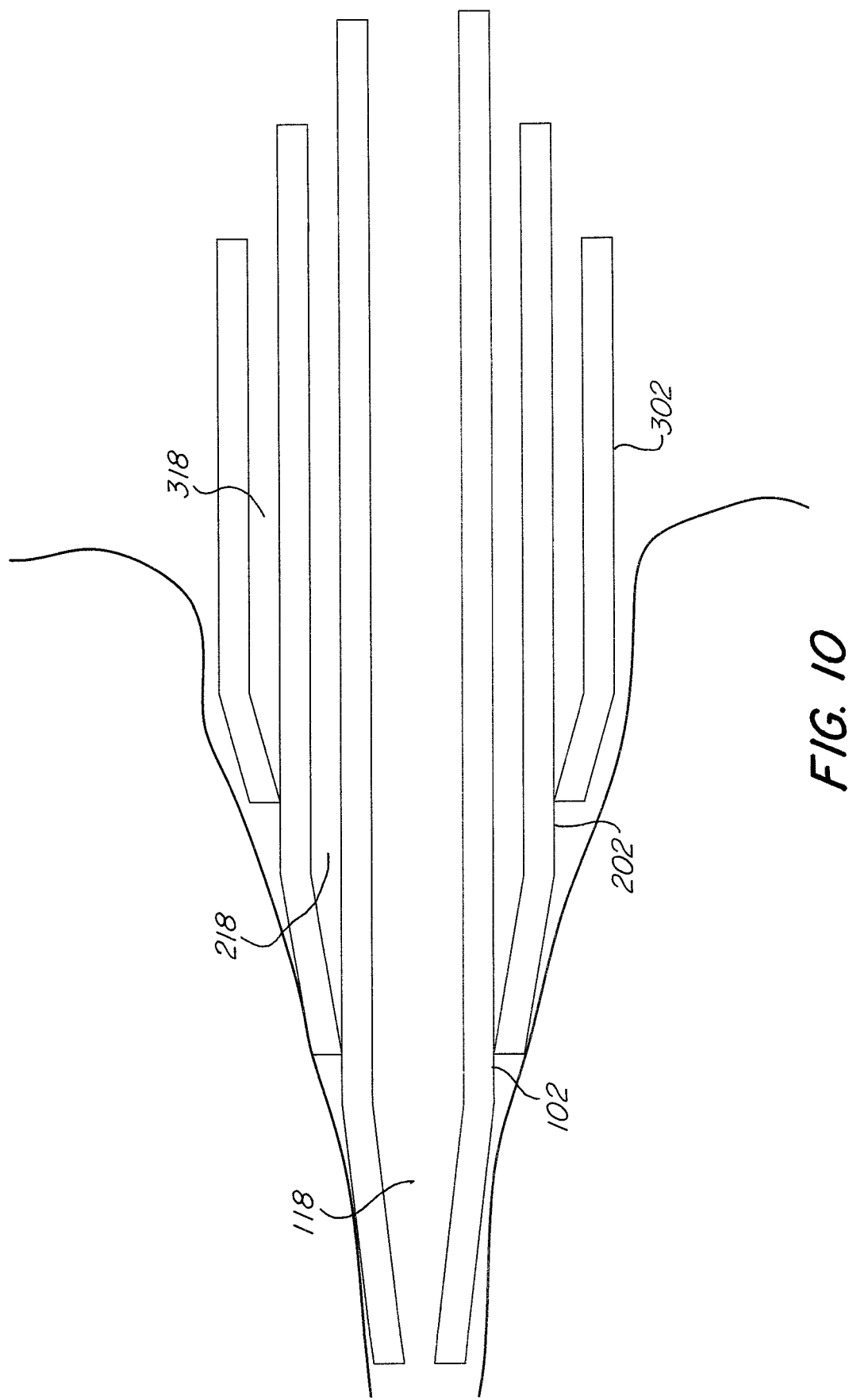
Figure 11:
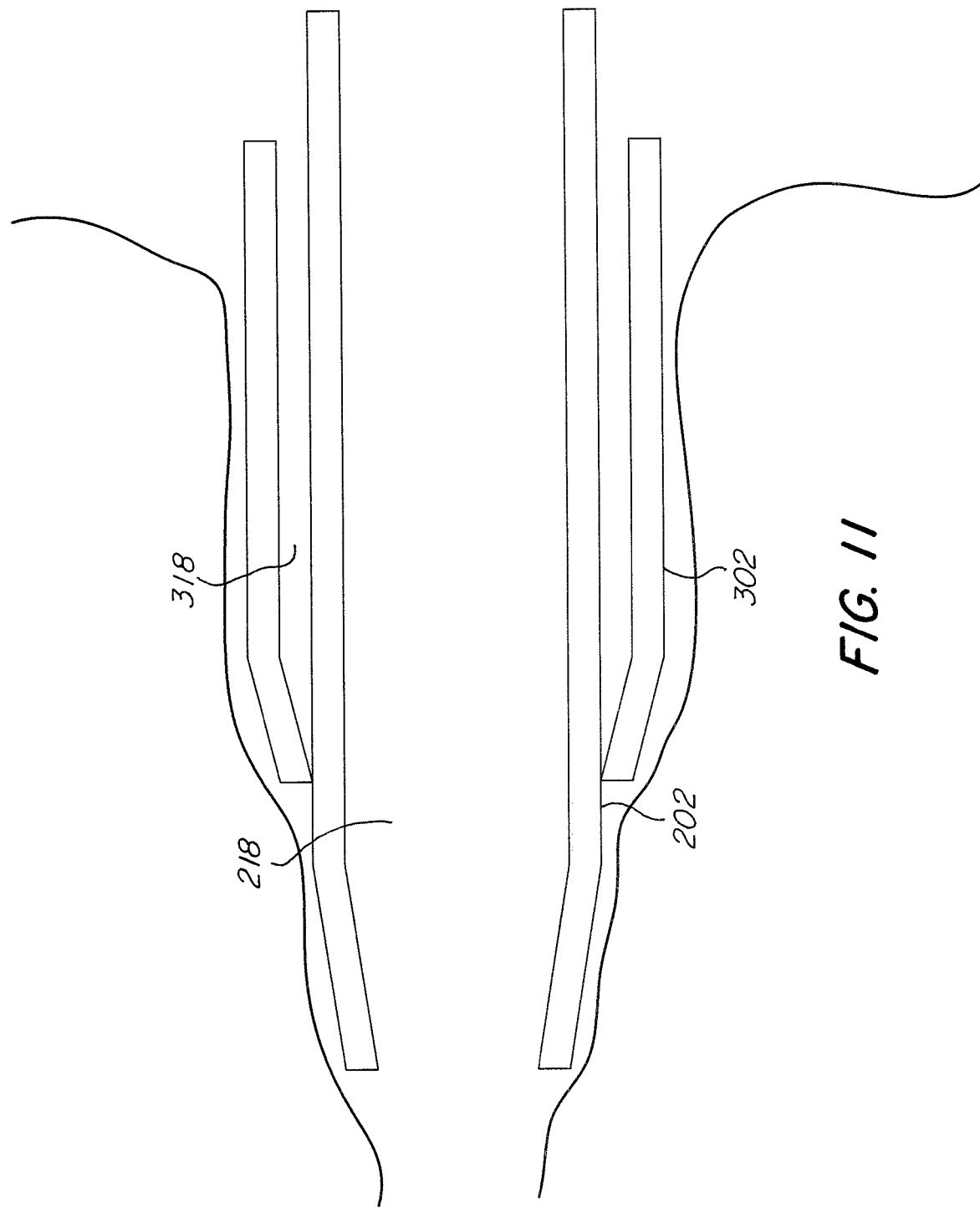
Figure 12:
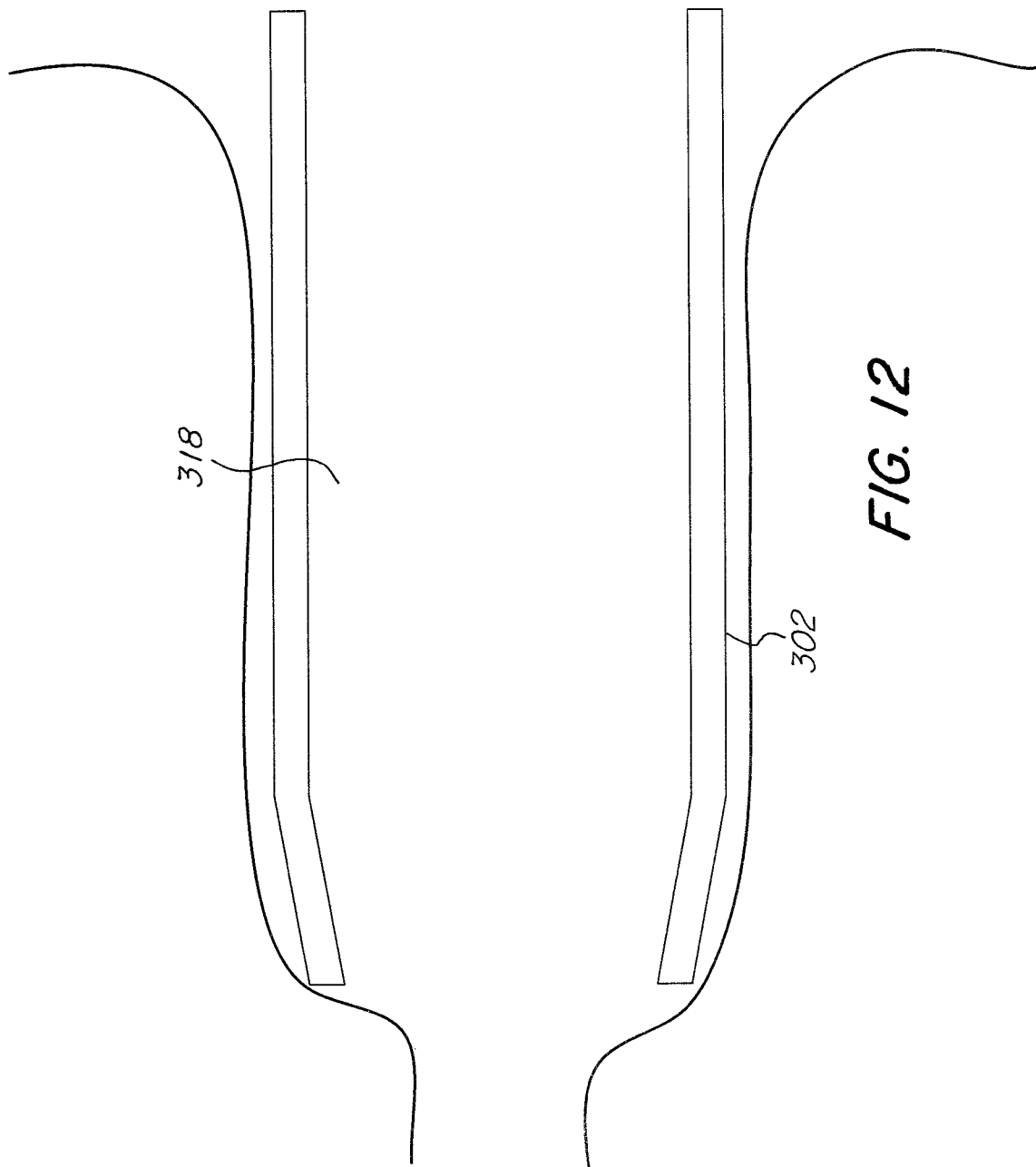

FIG. 9 illustrates the device advanced further into the body cavity, while FIG. 10 illustrates the device advanced such that the third member is introduced into the body cavity. FIG. 11 shows the second member advanced into the body cavity while the first member has been withdrawn allowing for a larger working channel 218 to be utilized as desired. All of the previously described procedures may be accomplished in second channel 218. Finally, FIG. 12 shown the third member 300 advanced in the body cavity and the second member 200 withdrawn. This provides yet a larger working cavity for the physician to perform any of the previously described procedures.

It is contemplated that the guard wires 230, 232, 330, 322 may be provided of a plastic material allowing the physician to cut the wires as desired to allow the various members to be advanced, one over the other into a desired position to facilitate the particular procedure. It should be noted that while dilation of the sinus ostia has been described herein, this device may effectively be used for dilation of virtually any body cavity to perform various medical procedures. Likewise, while FIGS. 8-12 have been described with reference to advancement of three members into the body cavity, it is contemplated that a fourth member may be utilized having a larger ID and OD than the third member allowing for an even larger working channel for performing various medical procedures.

Figure 13:
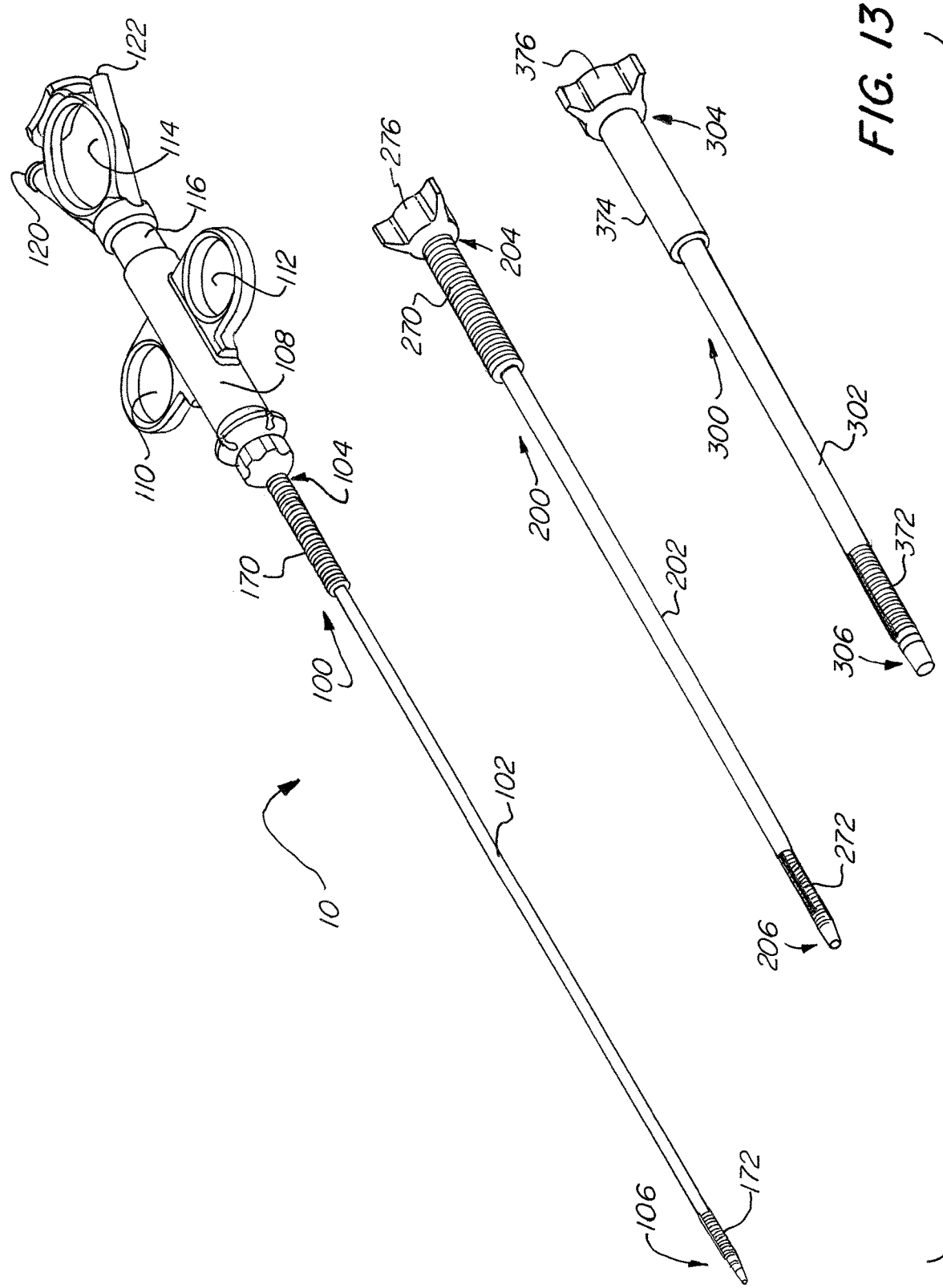
FIG. 13 is a perspective view of a device according to FIG. 1 in an unassembled condition.

Referring now to FIG. 13, the device 10 is depicted being similar to that shown in FIG. 1 with the exception that instead of showing the various guard wires, a screw-type of arraignment is shown for advancement of the of the second and third members 200, 300.

In FIG. 13, elongated body member 102 is depicted having threading 170 provided on an outer area of proximal end 104 and threading 172 provided on an outer area of distal end 106. The threading 170, 172 is designed to interact or engage with threading positioned on an interior of cavity 218, both at distal end 206 and proximal end 204.

Likewise, elongated body member 202 is depicted having threading 270 provided on an outer area of proximal end 204 and threading 272 provided on an outer area of distal end 206. The threading 270, 272 is designed to interact or engage with threading positioned on an interior of cavity 318, both at distal end 306 and proximal end 304.

Finally, elongated body member 302 is depicted having threading 272 provided on an outer area of distal end 306 and a sleeve 374 positioned at the proximal end 304, which may include threading on an interior surface of sleeve 374.

The functioning of the device 10 of this example is described below. The first member 100 is inserted into channel 218 of second member 200 to the point where the threading 170, 172 of the first member contacts the threading positioned on the inner surface of channel 218. The second member is then rotated to advance the second member 200 rearward (toward the handle 108) to a maximum amount allowed by the threading 170, 172.

A similar procedure is followed with respect to placing the second member within the channel 318 of the third member 300, which is again advanced rearward to a maximum amount allowed by threading 270, 272.

The device 10 is then ready for use for dilating a body cavity. To perform this procedure, the user advances the device 10 into a body cavity of the patient. First the distal end 106 of first member 100 is advanced to a desired location in the body cavity. Any number of procedures may be performed at this point as previously described in the application. At this point, the body cavity will be dilated to the O.D. of the first member 100.

The user may then advance the second member 200 over the first member 100 by turning knob 276 positioned at proximal end 204, which will function to advance the second member 200 further into the body cavity. The maximum amount of advancement will be determined by the threading 170, 172. The first member 100 may now be withdrawn from channel 218 such that any number of procedures may be performed at this point as previously described in the application. At this point, the body cavity will be dilated to the O.D. of the second member 200.

Finally, the user may then advance the third member 300 over the second member 200 by turning knob 376 positioned at proximal end 304, which will function to advance the third member 300 further into the body cavity. The maximum amount of advancement will be determined by the threading 270, 272. The second member 200 may now be withdrawn from channel 318 such that any number of procedures may be performed at this point as previously described in the application. At this point, the body cavity will be dilated to the O.D. of the third member 300.

The threading 372 and sleeve 374 are provided to interact with a fourth member (not shown) that may be slid over the top of third member 300 to provide another member to dilate the body cavity even further if necessary. As discussed in connection with the first member 100 and the second member 200, the third member 300 could be removed leaving an even larger working channel in the fourth member for any of the various procedures to be performed as described in the application.

Again, the threaded arraignment depicted in FIG. 13 allows for the precise advancement of the members into the body cavity as the user advances the members via knobs 276, 376. It is also contemplated that measurement indications may be provided to provide a visual indication to the user of how far a member is advanced relative to another member.

Figure 14:
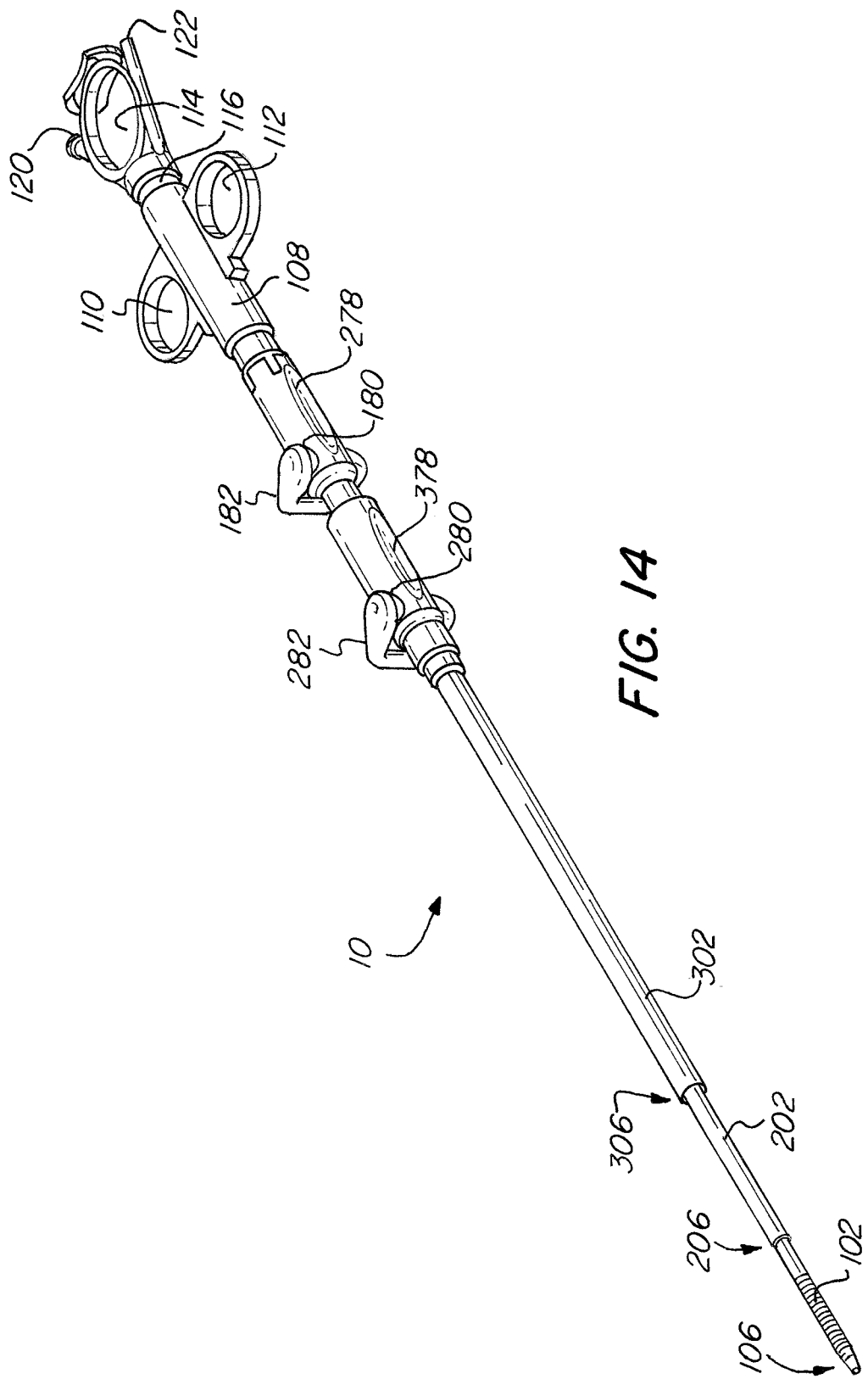
FIG. 14 is a perspective view of a device according to FIG. 1.
Figure 15:
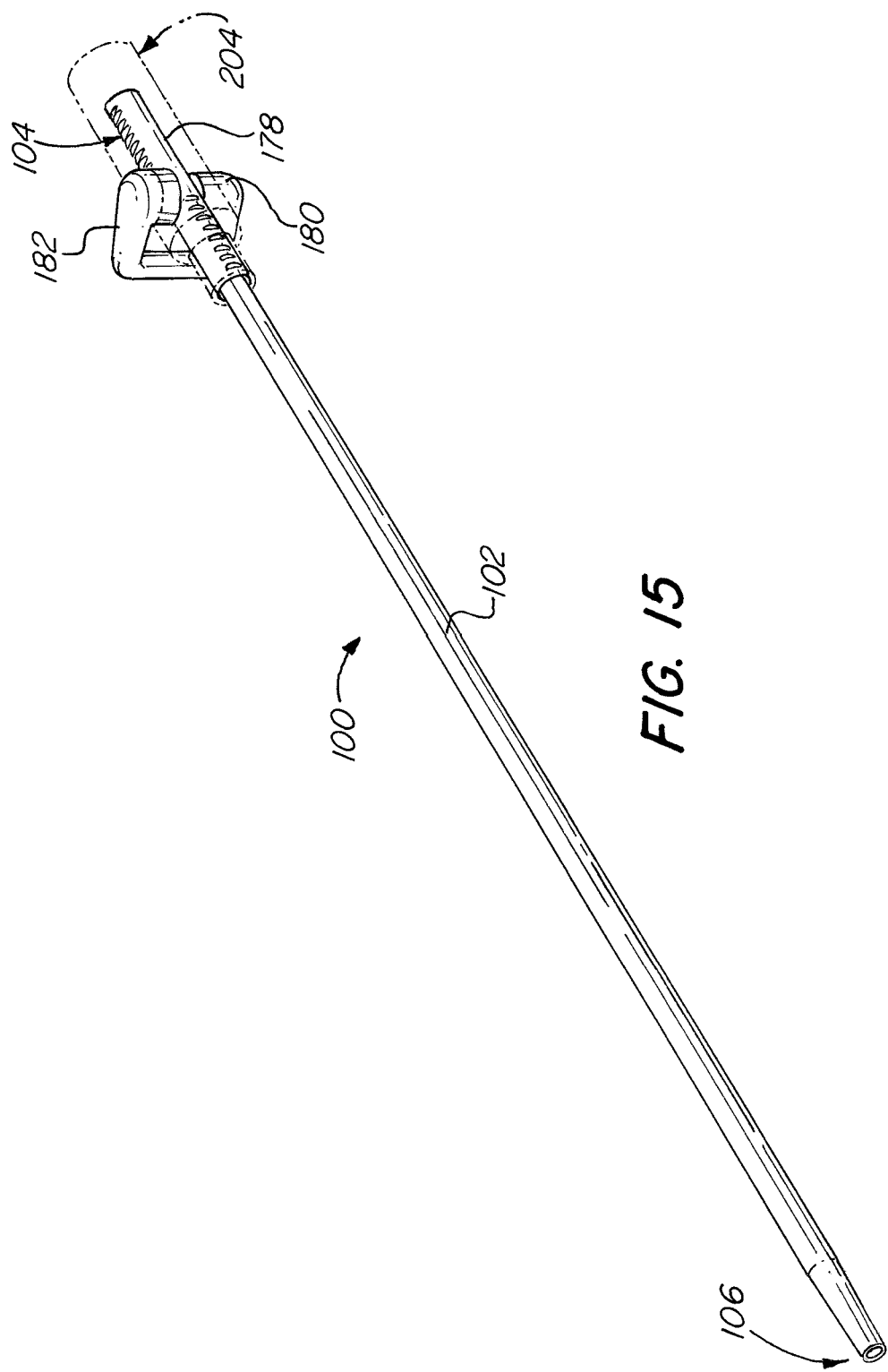
FIGS. 15-16 are perspective views of the device according to FIG. 14.

Referring now to FIGS. 14-17, illustrates a similar configuration as previously described in connection with FIGS. 1 and 13, with the exception that the advancement system used comprises a ratchet configuration. For example, the assembled device is shown in FIG. 14 including the first member 100, the second member 200, and the third member 300.

Figure 16:
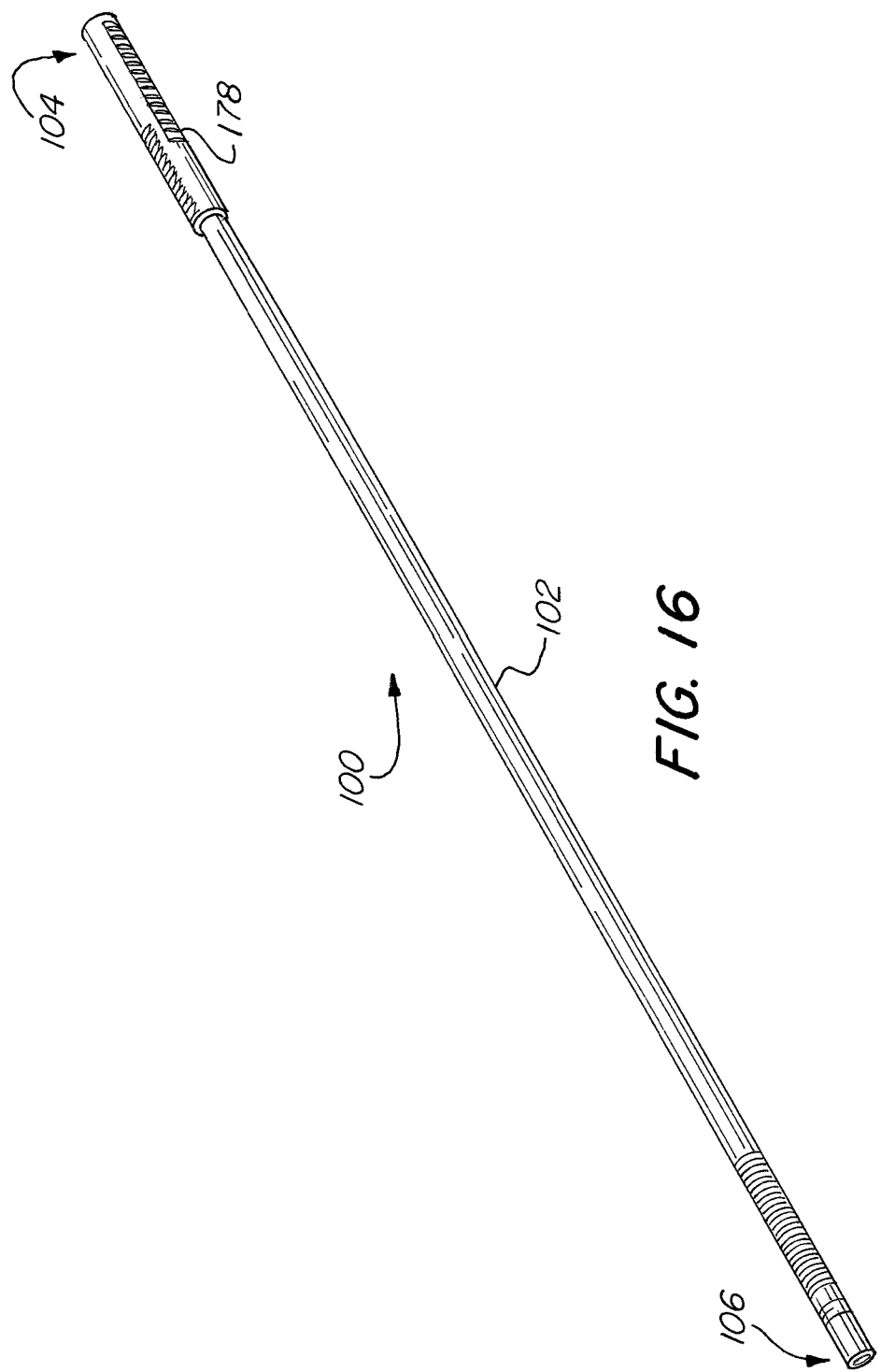
Figure 17:
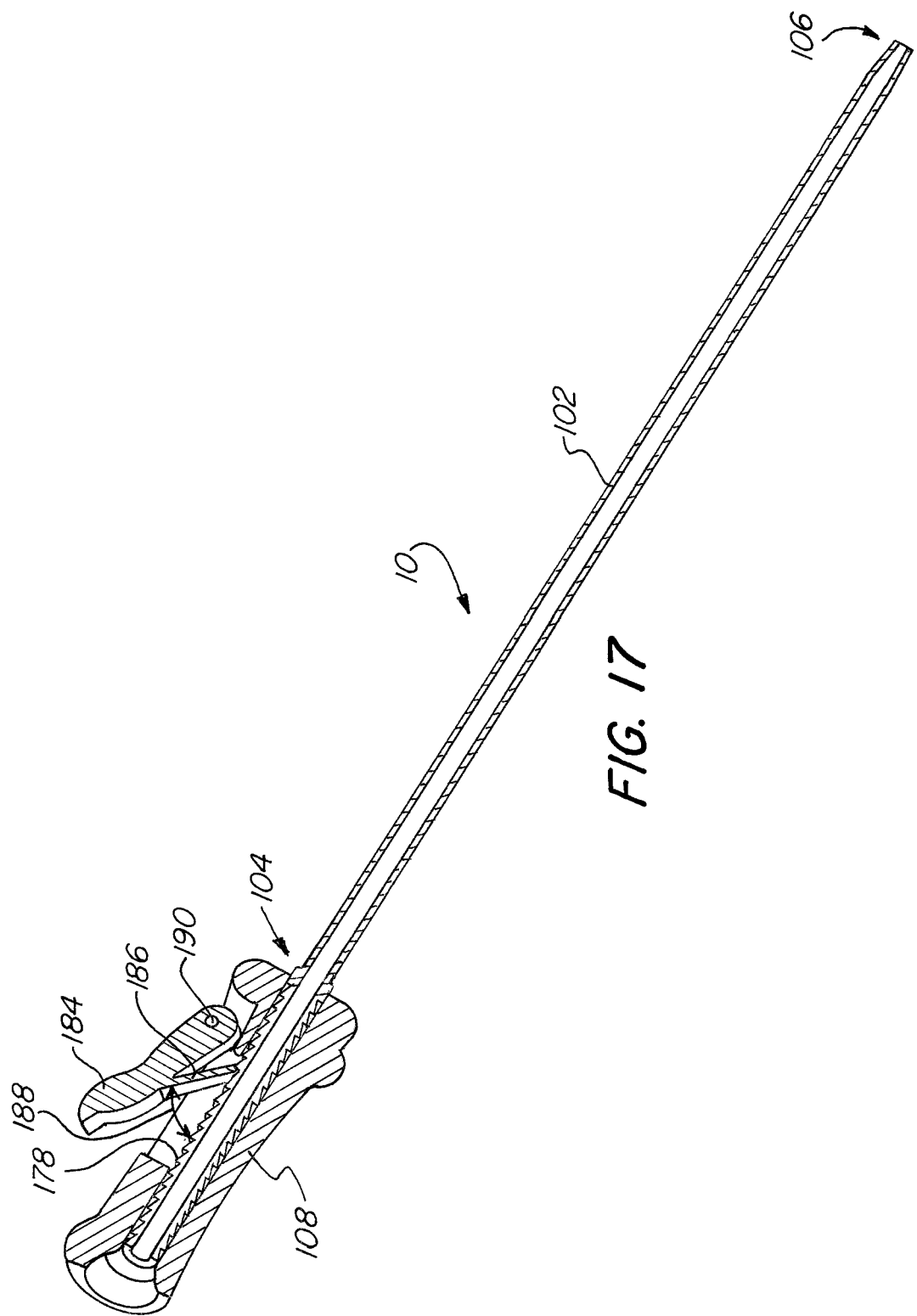
FIG. 17 is a perspective view of a device according to FIG. 14.

The racket system comprises a series of indentations 178 that are positioned on an exterior surface of elongated body member 102 at the proximal end 104 as illustrated in FIG. 16. The indentations 178 are provided to interact with a protrusion 186 (FIG. 17). In this arraignment, the handle 108 is provided with a lever 184 that is pivotally attached to the handle and includes a protrusion 186 that is designed to engage with indentations 178 that are positioned on an exterior surface of elongated body member 102 at the proximal end 104.

The protrusion 186 is provided at an acute angle 188 (which in one example may be approx. 45 degrees) relative to a longitudinal length of elongated body member 102. In this manner, when a user pushes down on the lever 184, the lever rotates about pivot point 190 downward toward the elongated body member 102. This rotational movement translates to linear displacement of elongated body member 102 relative to handle 108 as the protrusion 186 interacts with one of the indentations 178 to advance the elongated body member 102 into the body cavity. It is further contemplated that the lever 184 will be provided with a biasing force (e.g., a spring or the like) that, when the user releases the lever 184, will move the lever outwardly relative to the elongated body member 102 back to the original extended position. This rotation of the lever outwardly will function to move the protrusion 186 out of contact with the particular indentation 178 it was interacting with, and come in contact with the next indentation 178 in the series of indentations.

The user can then press down on lever 184 again and repeat the process described above to continue advancing the elongated body member 102 in a measured and incremental manner.

Thus far, advancement of the first member 100 relative to the handle 108 has been discussed. It will be further understood that the second member 200 may also be advanced in a measured and incremental manner relative to first member 100. This is achieved by providing indentations 278 on an exterior surface of second member 200, which are designed to interact with at least one protrusion 180 held by arm 182. The at least one protrusion is designed to interact with indentations 278 in a ratcheting manner thereby advancing second member 200 relative to first member 100.

In like manner, the third member 300 may also be advanced in a measured and incremental manner relative to second member 200. This is achieved by providing indentations 378 on an exterior surface of third member 300, which are designed to interact with at least one protrusion 280 held by arm 282. The at least one protrusion is designed to interact with indentations 378 in a ratcheting manner thereby advancing third member 300 relative to second member 200.

The additional structure and function of device 10 is similar as described in connection with FIGS. 1-12 and therefore will not be re-described here.

A primary benefit of the system disclosed herein is provision of a body cavity dilation system that allows for the dilation of a body cavity while at the same time, not posing the risk of cavity fracture associated with other dilation systems.

It is envisioned that the device 10 may be used in many differing procedures including, for example, tissue desiccation, removal of obstructive pathology, applying energy to a tissue, and reflecting energy to determine distance, size, shape and density of tissue. Likewise, the device 10 may be used for many differing types of applications including, for example, arthrectomy in a vasculature (e.g. plaque removal); urologic indications such as radical prostectomy, benign prostate hypertrophy or breaking up kidney stones; genecology such as remodeling of mucosal membranes or endometrial ablation; used in the lungs for dilatation and remodeling bronchial smooth tissues or muscles, denervating bronchial nerve; sinoplasty to treat chronic sinusitis; spinal applications for minimally invasive spine fusion procedures, spine stenosis procedures, modification the neural foreman, modification of the facet joint, etc.; and similar purposes as described above in relation to the gastroenterological tract.

Although the invention has been described with reference to a particular arrangement of parts, features and the like, these are not intended to exhaust all possible arrangements or features, and indeed many other modifications and variations will be ascertainable to those of skill in the art.

What is claimed is:
1. A device for dilating a body cavity comprising:
a first member including:
  a first elongated body portion with a first proximal end and a first distal end defining a first length, the first distal end being deflectable, said first elongated body portion defining a first outside diameter (OD) and having a first channel therein extending from the first proximal end to the first distal end, the first channel defining a first inside diameter (ID);
  a handle coupled to the first proximal end, said handle including a deflection control for deflection of the first distal end;
a second member including:
  a second elongated body portion with a second proximal end and a second distal end defining a second length, the second distal end being deflectable, said second elongated body portion defining a second OD and having a second channel therein extending from the second proximal end to the second distal end, the second channel defining a second ID and having a proximal second channel opening and a distal second channel opening;
said second ID being larger than the first OD such that said first member is longitudinally moveable within the second channel and, when said first elongated body portion is inserted in a body cavity and said second elongated body portion is advanced over said first elongated body portion, said cavity is dilated to the second OD;
the first distal end being moveable in a proximal direction through the distal second channel opening, through the second channel along the entire second length, and out through the proximal second channel opening;
a third member including:
  a third elongated body portion with a third proximal end and a third distal end defining a third length, the third distal end being deflectable, said third elongated body portion defining a third OD and having a third channel therein extending from the third proximal end to the third distal end, the third channel defining a third ID and having a proximal third channel opening and a distal third channel opening;
said third ID being larger than the second OD such that said second member is longitudinally moveable within the third channel and, when said second elongated body portion is inserted in a body cavity and said third elongated body portion is advanced over said second elongated body portion, said cavity is dilated to the third OD;

the second distal end being moveable in a proximal direction through the distal third channel opening, through the third channel along the entire third length, and out through the proximal third channel opening; and a wireless energy generator coupled to any of said first, second or third channels such that wireless energy is transmitted through the respective first, second or third channels;

wherein at least one of the first, second and third distal ends has plurality of fenestrations passing through a circumferential wall thereof, and the wireless energy is transmitted to the body cavity via the plurality of fenestrations.

2. The device according to claim 1 wherein the wireless energy is ultrasonic energy.

3. The device according to claim 1 wherein the second length is less than the first length and the third length is less than the second length.

4. The device according to claim 1 wherein the first, second and third distal ends are tapered.

5. The device according to claim 1 wherein said first member is detachable from said second member, and said second member is detachable from said third member.

6. The device according to claim 1 further comprising:
a light source for generating illuminating light to illuminate and area ahead of the first distal end;
an imaging device for receiving reflected light from the area ahead of the first distal end and generating image data based on the received light; and
a display for displaying the image data.

7. The device according to claim 6 wherein said light source and said imaging device are positioned at the first distal end.

8. The device according to claim 6 further comprising a power source positioned in said handle and coupled to said light source and said imaging device.

9. The device according to claim 1 further comprising an irrigation device providing an irrigation fluid to the body cavity through any of: the first channel, the second channel or the third channel.

10. The device according to claim 1 further comprising an aspiration device aspirating a fluid from the body cavity through any of: the first channel, the second channel or the third channel.

11. The device according to claim 1 wherein the second and third proximal ends each comprise a flange.

12. The device according to claim 1 wherein the handle comprises at least one finger hole wherein the deflection control is operated by depression of a plunger.

13. The device according to claim 1 further comprising a drug delivery device providing a drug to the body cavity through any of: the first channel, the second channel or the third channel.

14. The device according to claim 1 wherein
said first member includes threading positioned on an exterior surface of the first elongated member;
said second member includes threading positioned on an interior surface of the second channel and an exterior surface of the second elongated member;
said third member includes threading positioned on an interior surface of the third channel of the third elongated member.

15. The device according to claim 14 further comprising a first knob that when turned advances the second member with respect to the first member via the threading on the exterior surface of the first member interacting with the threading on the interior surface of the second member.

16. The device according to claim 15 further comprising a second knob that when turned advances the third member with respect to the second member via the threading on the exterior surface of the second member interacting with the threading on the interior surface of the third member.

17. The device according to claim 1 wherein the handle includes:
a lever having a protrusion that is designed to interact with indentations provided on an exterior surface of the first member,
wherein actuation of said lever causes said lever to rotate about an axis thereby causing the protrusion to contact one of the indentations to translate the rotational movement of said lever into linear displacement of the first member relative to the handle.

18. The device according to claim 1 wherein the wireless energy is RF energy.

19. The device according to claim 1 wherein the first distal end has the plurality of fenestrations passing through the circumferential wall thereof.

20. The device according to claim 1 wherein the third distal end has the plurality of fenestrations passing through the circumferential wall thereof.

21. The device according to claim 1 wherein the second distal end has the plurality of fenestrations passing through the circumferential wall thereof.

22. The device according to claim 1 wherein the first, second and third distal ends have the fenestrations passing through the circumferential walls thereof.

23. The device according to claim 1 wherein the fenestrations are axially displaced from one another along the distal tip.

24. The device according to claim 23 wherein the fenestrations are radially displaced from one another around the distal tip.

25. The device according to claim 1 wherein the fenestrations are radially displaced from one another around the distal tip.

* * * * *